(12) United States Patent
Anderskewitz et al.

(10) Patent No.: US 6,489,359 B2
(45) Date of Patent: Dec. 3, 2002

(54) SULPHOXYBENZAMIDES

(75) Inventors: Ralf Anderskewitz, Bingen (DE); Kurt Schromm, Ingelheim (DE); Franz Birke, Ingelheim (DE); Hans Michael Jennewein, Wiesbaden (DE)

(73) Assignee: Boehringer Ingelheim Pharma KG, Ingelheim (DE)

( * ) Notice: Subject to any disclaimer, the term of this patent is extended or adjusted under 35 U.S.C. 154(b) by 0 days.

(21) Appl. No.: 10/050,076

(22) Filed: Oct. 23, 2001

(65) Prior Publication Data

US 2002/0161043 A1 Oct. 31, 2002

Related U.S. Application Data

(60) Provisional application No. 60/250,501, filed on Dec. 1, 2000.

(30) Foreign Application Priority Data

Dec. 1, 2000 (DE) .......................................... 100 52 333

(51) Int. Cl.$^7$ ...................... A61K 31/155; C07C 305/24
(52) U.S. Cl. .......................................... 514/517; 558/37
(58) Field of Search ............................. 558/37; 514/517

(56) References Cited

U.S. PATENT DOCUMENTS

| | | | |
|---|---|---|---|
| 6,127,423 A | 10/2000 | Anderskewitz et al. | |
| 6,197,824 B1 | 3/2001 | Schromm et al. | |
| 6,265,612 B1 * | 7/2001 | Schromm et al. | 564/244 |

* cited by examiner

*Primary Examiner*—Flona T. Powers
(74) *Attorney, Agent, or Firm*—Robert P. Raymond; Philip I. Datlow; Alan R. Stempel

(57) ABSTRACT

The present invention relates to new sulphoxybenzamides of general formula I, processes for preparing them as well as their use as medicaments

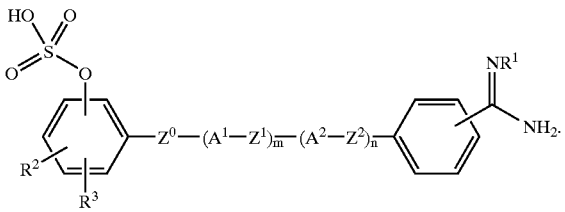

11 Claims, No Drawings

SULPHOXYBENZAMIDES

RELATED APPLICATIONS

Benefit of U.S. Provisional Application Ser. No. 60/250,501, filed on Dec. 1, 2000 is hereby claimed, and said Application is herein incorporated by reference.

FIELD OF THE INVENTION

The present invention relates to new sulphoxybenzamides of formula I, (I)

wherein the groups $R^1$, $R^2$, $R^3$, $A^1$, $A^2$, $Z^0$, $Z^1$, $Z^2$, m and n have the meanings given in the claims and specification, processes for preparing them as well as their use as medicaments, particularly as leukotriene $B_4$ ($LTB_4$) antagonists.

BACKGROUND TO THE INVENTION

Benzamidine derivatives are known from the prior art as active substances with valuable pharmaceutical properties. Thus, for example, International Patent Applications WO 97/21670 (corresponding to U.S. Pat. No. 6,127,423) and WO 98/11062 (corresponding to U.S. Pat. No. 6,197,824 B1) disclose inter alia benzamidines which have free hydroxy groups. They contain no references of any kind to benzamidines containing sulphate groups.

The aim of the present invention is to prepare new $LTB_4$ antagonists which, by virtue of their $LTB_4$ antagonistic properties, have many possible uses in the therapeutic field.

DETAILED DESCRIPTION OF THE INVENTION

Surprisingly, it has been found that benzamidine derivatives containing sulphate groups, of general formula (I)

(I)

wherein the groups $R^1$, $R^2$, $R^3$, $A^1$, $A^2$, $Z^0$, $Z^1$, $Z^2$, m and n have the meanings given in the claims and specification, have an $LTB_4$ antagonistic activity and may be used according to the invention for the prevention and treatment of diseases in which $LTB_4$ antagonists may provide a therapeutic benefit.

The invention thus relates to sulphoxybenzamides of general formula I wherein $Z_0$ denotes a group selected from the formulae —$X^1$—$(CH_2)_r$—$X^2$— and —$CR^4R^5$—, $A^1$ and $A^2$ independently of one another each denote a 1,4-phenylene- or 1,3-phenylene group optionally substituted by one or more halogen atoms, $C_1$–$C_8$-alkyl groups, $C_2$–$C_8$-alkenyl groups, $C_1$–$C_8$-haloalkyl groups or $C_1$–$C_8$-alkoxy groups, $Z^1$ and $Z^2$ independently of one another each denote a group of formula —$X^3$—$(CH_2)_s$—$X^4$— or a single bond, $R^1$ denotes hydrogen, hydroxy, —COO—$C_1$–$C_8$-alkyl or —COO—$C_1$–$C_4$-alkyl-phenyl, whilst in the above-mentioned group the phenyl ring in each case may be substituted by $C_1$–$C_4$-alkyl or $C_1$–$C_4$-alkoxy, $R^2$ and $R^3$ independently of one another each denote a hydrogen or halogen atom, or a $C_1$–$C_8$-alkyl, $C_1$–$C_8$-haloalkyl, $C_1$–$C_8$-alkoxy, aryl, aryloxy or aralkyl group, $R^4$ and $R^5$ independently of one another each denote hydrogen or $C_1$–$C_4$-alkyl, $X^1$ and $X^2$ independently of one another each denote —O—, —S—, —NH— or a single bond, $X^3$ and $X^4$ independently of one another each denote —O—, —S—, —NH— or a single bond, m and n independently of one another each denote 0 or 1, and r and s independently of one another denote an integer from 1 to 8, optionally in the form of the tautomers, racemates, enantiomers, diastereomers and mixtures thereof, as well as optionally the pharmacologically acceptable salts thereof.

Preferred compounds are those of formula I wherein $Z^0$ denotes a group selected from the formulae —$X^1$—$(CH_2)_r$—$X^2$— and —$CR^4R^5$—, $A^1$ and $A^2$ independently of one another each denote a 1,4-phenylene or 1,3-phenylene group optionally substituted by a $C_1$–$C_4$-alkyl group or $C_2$–$C_4$-alkenyl group, $Z^1$ and $Z^2$ independently of one another each denote a group of formula —$X^3$—$(CH_2)_s$—$X^4$— or a single bond, $R^1$ denotes hydrogen, $R^2$ and $R^3$ each denote a hydrogen atom, $R^4$ and $R^5$ independently of one another each denote $C_1$–$C_4$-alkyl, $X^1$ and $X^2$ independently of one another each denote —O— a single bond, $X^3$ and $X^4$ independently of one another each denote —O— or a single bond, m and n independently of one another each denote 0 or 1, and r and s independently of one another each denote an integer from 1 to 3.

Another preferred embodiment comprises the compounds of formula I, wherein $Z^0$ denotes a group of formula —$CR^4R^5$—, $A^1$ and $A^2$ independently of one another each denote a 1,4-phenylene or 1,3-phenylene group optionally substituted by a $C_1$–$C_4$-alkyl group or $C_2$–$C_4$-alkenyl group, and preferably $A^1$ denotes 1,4-phenylene and $A^2$ denotes 1,3-phenylene, $Z^1$ and $Z^2$ independently of one another each denote a group of formula —$X^3$—$(CH_2)_s$—$X^4$—, and preferably $Z^1$ denotes —O—$CH_2$— and $Z^2$ denotes —$CH_2$—O—

$R^1$ denotes hydrogen, $R^2$ and $R^3$ each denote a hydrogen atom, $R^4$ and $R^5$ each denote methyl, $X^3$ and $X^4$ independently of one another each denote —O— or a single bond, m and n each denote 1, and s denotes 1.

Also preferred are compounds of formula I wherein $Z^0$ denotes a group of formula —$X^1$—$(CH_2)_r$—$X^2$—, $A^2$ denotes a 1,4-phenylene group substituted by a $C_1$–$C_4$-alkyl group or $C_2$–$C_4$-alkenyl group, preferably a 1,4-phenylene group substituted by an n-propyl or allyl group, $Z^2$ denotes a single bond, $R^1$ denotes hydrogen, $R^2$ and $R^3$ each denote a hydrogen atom, $X^1$ and $X^2$ independently of one another each denote —O—, m denotes 0, n denotes 1, and r denotes 2.

Unless specifically stated otherwise, the general definitions are used in the following sense: $C_1$–$C_8$-alkyl and $C_1$–$C_4$-alkyl generally denote a branched or unbranched hydrocarbon group with 1 to 4 or 8 carbon atom(s), which may optionally be substituted by one or more halogen atom(s), preferably flu orine, which may be identical to or different from one another. The following hydrocarbon groups are mentioned as examples:

methyl, ethyl, n-propyl, 1-methylethyl (isopropyl), n-butyl, 1-methylpropyl, 2-methylpropyl, 1,1-dimethylethyl, n-pentyl, 1-methylbutyl, 2-methylbutyl, 3-methylbutyl, 1,1-dimethylpropyl, 1,2-dimethylpropyl, 2,2-dimethylpropyl, 1-ethylpropyl, n-hexyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl. Unless otherwise stated, lower alkyl groups with 1 to 4 carbon atoms are preferred, such as methyl; ethyl, n-propyl, iso-propyl, n-butyl, 1-methylpropyl, 2-methylpropyl or 1,1-dimethylethyl.

$C_2$–$C_8$-alkenyl and $C_2$–$C_4$-alkenyl generally denote a branched or unbranched unsaturated hydrocarbon group with 2 to 4 or 8 carbon atom(s), which may optionally be substituted by one or more halogen atom(s), preferably fluorine, which may be identical to or different from one another. The following hydrocarbon groups are mentioned as examples:

Vinyl, allyl, prop-1-enyl, butenyl, pentenyl, hexenyl, heptenyl and octenyl. Unless otherwise stated, lower alkenyl groups with 2 to 4 carbon atoms, such as vinyl or allyl, are preferred.

The group —$(CH_2)_r$— or —$(CH_2)_s$— denotes a branched or unbranched double-bonded hydrocarbon bridge with 1 to 8 carbon atoms, which may optionally be substituted by one or more halogen atom(s), preferably fluorine, which may be identical to or different from one another.

Aryl generally denotes an aromatic group with 6 to 10 carbon atoms, preferably phenyl, while the aromatic group may be substituted by one or more lower alkyl group(s), lower alkenyl group(s), trifluoromethyl group(s), cyano group(s), alkoxy group(s), nitro group(s), amino group(s) and/or one or. more halogen atom(s), which may be identical or different; the preferred aryl group is an optionally substituted phenyl group, the preferred substituents being halogen—such as fluorine, chlorine or bromine—as well as hydroxyl.

Alkoxy generally denotes a straight-chain or branched hydrocarbon group with 1 to 8 carbon atom(s) bound via an oxygen atom. A lower alkoxy group with 1 to 3 carbon atom(s) is preferred. The methoxy group is particularly preferred.

Aryloxy generally denotes an aromatic group with 6 to 10 carbon atoms bound via an oxygen, preferably phenoxy, whilst the aromatic group may be substituted by one or more lower alkyl group(s), lower alkenyl group(s), trifluoromethyl group(s), cyano group(s), alkoxy group(s), nitro group (s), amino group(s) and/or one or more halogen atom(s), which may be identical or different; the preferred aryl group is an optionally substituted phenyl group, the preferred substituents being halogen—such as fluorine, chlorine or bromine—as well as hydroxyl.

Aralkyl generally denotes a aromatic group with 6 to 10 carbon atoms bound via an alkylene group, preferably phenylalkyl, whilst the aromatic group may be substituted by one or more lower alkyl group(s), lower alkenyl group(s), trifluoromethyl group(s), cyano group(s), alkoxy group(s), nitro group(s), amino group(s) and/or one or more halogen atom(s), which may be identical or different; the preferred aryl group is an optionally substituted phenyl group, the preferred substituents being halogen—such as fluorine, chlorine or bromine—as well as hydroxyl. The alkylene group is generally a double-bonded hydrocarbon bridge with 1 to 8 carbon atoms, preferably 1 to 3 carbon atoms, optionally substituted by one or more halogen atom(s)—preferably fluorine—which may be identical to or different from one another.

Most particularly preferred compounds are those of formulae IA and IB,

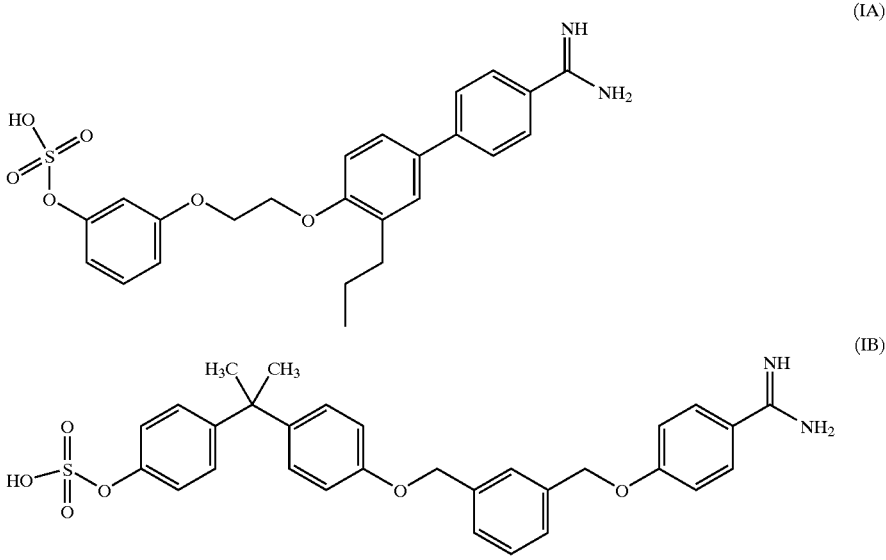

The compounds IA and IB may be formed in vivo as metabolites of a corresponding $LTB_4$-antagonistic compound with a free hydroxy group and exhibit the following $K_i$ values in the receptor binding test:

| Compound | $K_i$ [nM] |
|---|---|
| IA | 3.2 |
| IB | 40.0 |

As has been found, the compounds of formula I are characterised by their versatility of use in the therapeutic field. Particular emphasis should be laid on those applications for which the $LTB_4$-receptor-antagonistic properties play a part.

The following should be mentioned in particular: arthritis, asthma, chronic obstructive lung diseases such as chronic bronchitis, psoriasis, ulcerative colitis, gastro- or enteropathy induced by nonsteroidal antiphlogistics, cystic or pulmonary fibrosis, Alzheimer's disease, shock, reperfusion damage/ischaemia such as stroke or cardiac infarct, atherosclerosis, multiple sclerosis, autoimmune diseases, malignant neoplasia, alveolitis.

The new compounds may also be used to treat illnesses or conditions in which the passage of cells from the blood through the vascular endothelium into the tissues is of importance (such as metastasis) or illnesses and conditions in which the combination of $LTB_4$ or another active substance (such as 12-HETE) with the $LTB_4$ receptor has an influence on cell proliferation (e.g. chronic myeloid leukaemia).

The new compound may also be used in conjunction with other active substances, e.g. those which are used for the same indications, or e.g. with antiallergic agents, secretolytics, $\beta_2$-adrenergics, steroids taken by inhalation, antihistamines, $PDE_4$ inhibitors, peptido-leukotriene antagonists and/or PAF antagonists. They may be administered topically, orally, transdermally, nasally, parenterally or by inhalation.

The activity can be investigated pharmacologically and biochemically using tests as disclosed for example in WO 93/16036, pp. 15 to 17; reference is hereby made to the contents of this publication.

The therapeutic or prophylactic dose depends—apart from the potency of the individual compounds and the patient's body weight—on the nature and gravity of the condition. For oral administration the dosage is between 10 and 500 mg, preferably between 20 and 250 mg. By inhalation the amount of active substance delivered to the patient is between about 0.5 and 25, preferably between about 2 and 20 mg.

Solutions for inhalation generally contain between about 0.5 and 5% of active substance. The new compounds may be administered in conventional preparations, e.g. as plain or coated tablets, capsules, lozenges, powders, granules, solutions, emulsions, syrups, aerosols for inhalation, ointments and suppositories.

The following Examples show some possible ways of formulating the preparations:

EXAMPLES OF FORMULATIONS

1. Tablets

Composition:

| | |
|---|---|
| Active substance according to the invention | 20 parts by weight |
| Stearic acid | 6 parts by weight |
| Glucose | 474 parts by weight |

The ingredients are processed in the usual way to form tablets weighing 500 mg. If desired, the active substance content may be increased or reduced and the quantity of glucose reduced or increased accordingly.

| 2. Suppositories | |
|---|---|
| Composition: | |
| Active substance according to the invention | 100 parts by weight |
| Powdered lactose | 45 parts by weight |
| Cocoa butter | 1555 parts by weight |

The ingredients are processed in the usual way to form suppositories weighing 1.7 g.

3. Powder for inhalation

Micronised powdered active substance (compound of formula I; particle size about 0.5 to 7 μm) is packed into hard gelatine capsules in quantities of 5 mg, optionally with the addition of micronised lactose. The powder is inhaled from conventional inhalers, e.g. according to DE-A 33 45 722, to which reference is hereby made.

The compounds according to the invention compound are prepared using methods known per se from the prior art.

Thus, the compounds of general formula I may be prepared by reacting the benzamides of formula II which contain hydroxy groups:

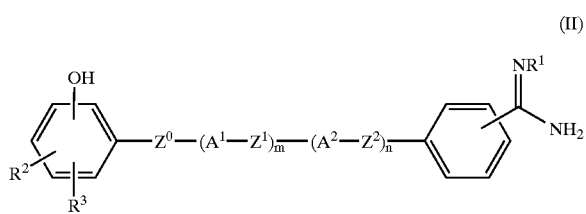
(II)

which are known, for example, from International Patent Applications WO 97/21670 (corresponding to U.S. Pat. No. 6,127,423) and WO 98/11062 (corresponding to U.S. Pat. No. 6,197,824 B1), wherein $Z^0$, $A^1$, $A^2$, $Z^1$, $Z^2$, $R^1$, $R^2$, $R^3$, m and n are as hereinbefore defined, with a sulphuric acid derivative of formula III, $$HO_3S-X \quad (III)$$

wherein X denotes a leaving group which may be substituted by a phenol oxygen, preferably a halogen atom, particularly chlorine, preferably in the presence of a weak base and a metal iodide.

In a preferred embodiment of the process according to the invention a compound of formula II or an acid addition salt thereof is reacted with a sulphuric acid derivative of formula III, particularly chlorosulphonic acid, in an inert diluent and in the presence of a base, or in a basic solvent such as, for example, triethylamine or pyridine, and in the presence of catalytic amounts of a metal iodide, preferably an alkali metal iodide, particularly potassium iodide, at a temperature of from −80 to +120° C., preferably from −40 to +100° C., particularly from −10 to +80° C. Under these preferred conditions the reaction is generally complete in 2 to 36 hours, preferably 4 to 18 hours.

The compound according to the invention may be prepared, starting from compounds known from the prior art, using the processes described in the following Examples, inter alia. Various other embodiments of the process will be apparent to anyone skilled in the art from the present specification. It is specifically pointed out, however, that these Examples and the related description are provided solely as an illustration and are not to be regarded as restricting the invention.

EXAMPLE 1

Benzenecarboximidamides, 4-[[3-[[4-[1-methyl-1-[4-(sulphoxy)phenyl]ethyl]phenoxy]methyl]phenyl]methoxy]

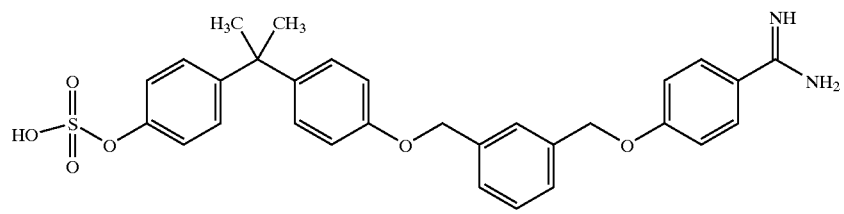

7.54 g of benzenecarboximidamides, [[4-[[3-[[4-[1-(4-hydroxyphenyl)-1-methylethyl]phenoxy]methyl]phenyl]methoxy], monohydrochloride were taken up in 200 ml of pyridine and combined with 4.0 g of chlorosulphonic acid (slowly added at ambient temperature) as well as a trace of potassium iodide. The mixture was stirred for 6 h at 60° C. Then the reaction mixture was carefully added to water, the precipitate was suction filtered and washed with methanol. Yield: 4.0 g (m.p. 284° C.).

EXAMPLE 2

[1,1'-Biphenyl]-4-carboximidamides, 3'-propyl-4'-[2-[3-(sulphoxy)phenoxy]ethoxy]

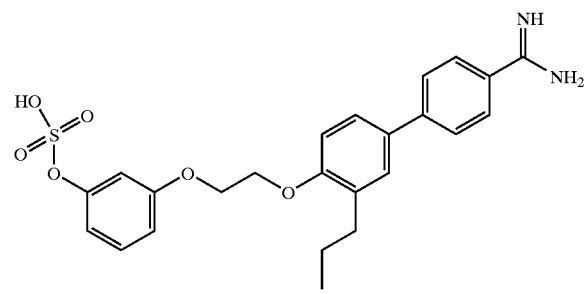

2.43 g of [1,1'-Biphenyl]-4-carboximidamides, 4'-[2-(3-hydroxyphenoxy)ethoxy]-3'-propyl, monomethanesulphonate, 100 ml of pyridine and 0.1 g of potassium iodide were combined and 1.5 g of chlorosulphonic acid were slowly added dropwise with stirring. The mixture was stirred for 6 hours at 50–60° C. After cooling the mixture was added to 1 liter of water, the crystals precipitated were suction filtered and recrystallised 2× from dimethylformamide. 1.25 g of white crystals. M.p.>270° C.

EXAMPLES 3–14

The following compounds

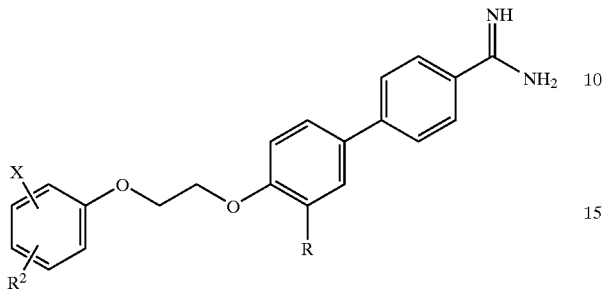

are prepared analogously to Examples 1 and 2 from the corresponding phenols:

| Example No. | X | $R^2$ | R |
|---|---|---|---|
| 3 | 4-$HO_3SO$— | H | n-$C_3H_7$ |
| 4 | 4-$HO_3SO$-phenyl | H | n-$C_3H_7$ |
| 5 | 4-$HO_3SO$— | 3-phenyl | n-$C_3H_7$ |
| 6 | 4-$HO_3SO$— | 2-n-$C_3H_7$ | n-$C_3H_7$ |
| 7 | 4-(4-$HO_3SO$-phenoxy)- | H | n-$C_3H_7$ |
| 8 | 4-[1-(4-$HO_2SO$-phenyl)-1-methyl]-ethyl | H | n-$C_3H_7$ |
| 9 | 4-[1-(4-$HO_2SO$-phenyl)-1-methyl]-ethyl | 2-n-$C_3H_7$ | n-$C_3H_7$ |
| 10 | 3-$HO_3SO$— | 2-n-$C_3H_7$ | n-$C_3H_7$ |
| 11 | 2-$HO_3SO$— | H | n-$C_3H_7$ |
| 12 | 5-$HO_3SO$— | 2-n-$C_3H_7$ | n-$C_3H_7$ |
| 13 | 3-$HO_3SO$— | 4-$CH_3$—O— | n-$C_3H_7$ |
| 14 | 3-$HO_3SO$— | H | $CH_2$=CH—$CH_2$— |

What is claimed is:

1. A compound of formula I

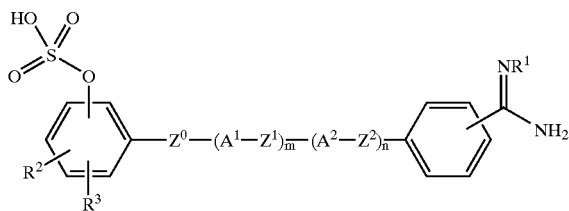

(I)

wherein $Z^0$ denotes a group selected from the formulae —$X^1$—$(CH_2)_r$—$X^2$— and —$CR^4R^5$—, $A^1$ and $A^2$ independently of one another each denote a 1,4-phenylene- or 1,3-phenylene group, each optionally substituted by one or more halogen atoms, $C_1$–$C_8$-alkyl groups, $C_2$–$C_8$-alkenyl groups, $C_1$–$C_8$-haloalkyl groups or $C_1$–$C_8$-alkoxy groups, $Z^1$ and $Z^2$ independently of one another each denote a group of formula —$X^3$—$(CH_2)_s$—$X^4$— or a single bond, $R^1$ denotes hydrogen, hydroxy, —COO—$C_1$–$C_8$-alkyl or —COO—$C_1$–$C_4$-alkyl-phenyl, wherein said phenyl group may be substituted by $C_1$–$C_4$-alkyl or $C_1$–$C_4$-alkoxy, $R^2$ and $R^3$ independently of one another each denote a hydrogen or halogen atom, or a $C_1$–$C_8$-alkyl, $C_1$–$C_8$-haloalkyl, $C_1$–$C_8$-alkoxy, aryl, aryloxy or aralkyl group, $R^4$ and $R^5$ independently of one another each denote hydrogen or $C_1$–$C_4$-alkyl, $X_1$ and $X^2$ independently of one another each denote —O—, —S—, —NH— or a single bond, $X^3$ and $X^4$ independently of one another each denote —O—, —S—, —NH— or a single bond, m and n independently of one another each denote 0 or 1, and r and s independently of one another each denote an integer from 1 to 8, optionally in the form of a tautomer, racemate, enantiomer, diastereomer and mixtures thereof, or a pharmacologically acceptable salt thereof.

2. A compound of formula I according to claim 1, wherein $Z^0$ denotes a group selected from the formulae —$X^1$—$(CH_2)_r$—$X^2$— and —$CR^4R^5$—, $A^1$ and $A^2$ independently of one another each denote a 1,4-phenylene or 1,3-phenylene group, each optionally substituted by a $C_1$–$C_4$-alkyl group or $C_2$–$C_4$-alkenyl group, $Z^1$ and $Z^2$ independently of one another each denote a group of formula —$X^3$—$(CH_2)_s$—$X^4$— or a single bond, $R^1$ denotes hydrogen, $R^2$ and $R^3$ each denote a hydrogen atom, $R^4$ and $R^5$ independently of one another each denote $C_1$–$C_4$-alkyl, $X_1$ and $X^2$ independently of one another each denote —O— or a single bond, $X^3$ and $X^4$ independently of one another each denote —O— or a single bond, m and n independently of one another each denote 0 or 1, and r and s independently of one another each denote an integer from 1 to 3.

3. A compound of formula I according to claim 2, wherein $Z^0$ denotes a group of formula —$X^1$—$(CH_2)_r$—$X^2$—, $A^2$ denotes a 1,4-phenylene group substituted by a $C_1$–$C_4$-alkyl or $C_2$–$C_4$-alkenyl group, $Z^2$ denotes a single bond, $R^1$ denotes hydrogen, $R^2$ and $R^3$ each denote a hydrogen atom, $X^1$ and $X^2$ independently of one another each denote —O—, m denotes 0,
n denotes 1, and
r denotes 2.

4. A compound of formula IA

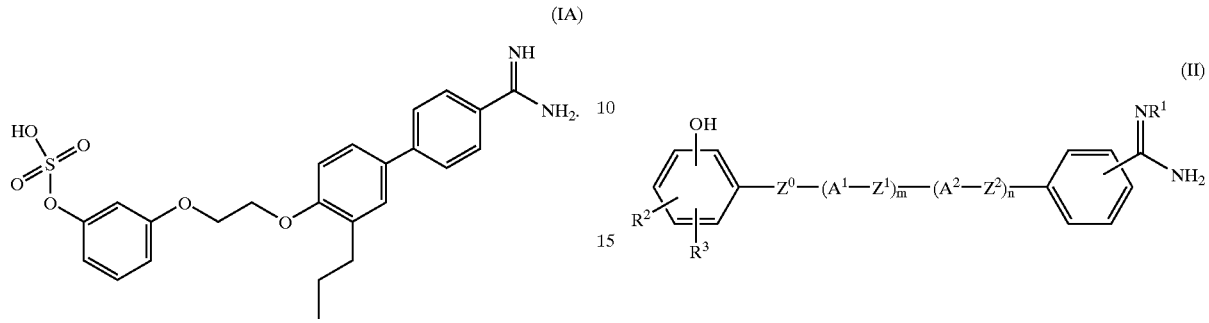

5. A compounds of formula I according to claim 2, wherein
$Z^0$ denotes a group of formula —$CR^4R^5$—,
$A^1$ and $A^2$ independently of one another each denote a 1,4-phenylene or 1,3-phenylene group, each optionally substituted by a $C_1$—$C_4$-alkyl group,
$Z^1$ and $Z^2$ independently of one another each denote a group of formula —$X^3$—$(CH_2)_s$—$X^4$—
$R^1$ denotes hydrogen,
$R^2$ and $R^3$ each denote a hydrogen atom,
$R^4$ and $R^5$ each denote methyl,
$X^3$ and $X^4$ independently of one another each denote —O— or a single bond,
m and n each denote 1, and
s denotes 1.

6. A compound of formula IB

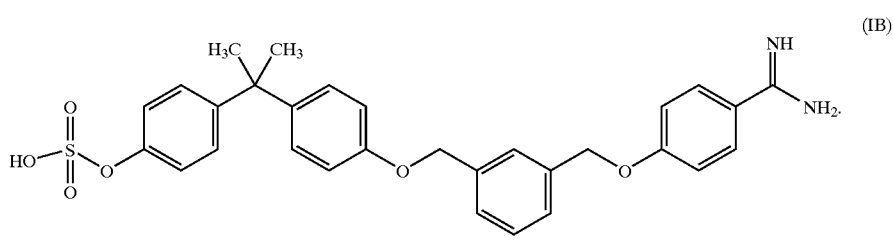

7. A process for preparing a compound of formula I, according to claim 1, wherein a hydroxybenzamidine of formula II

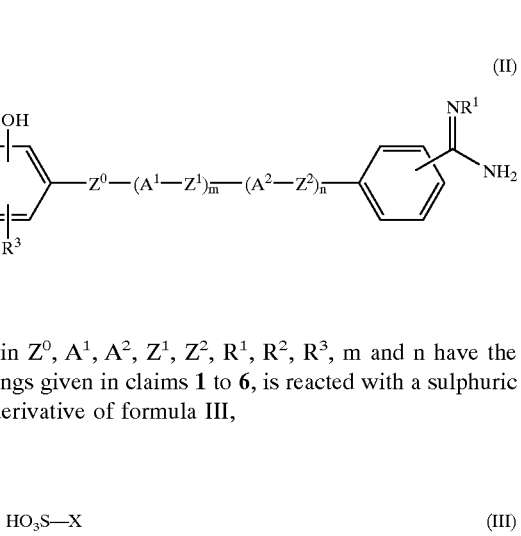

wherein $Z^0$, $A^1$, $A^2$, $Z^1$, $Z^2$, $R^1$, $R^2$, $R^3$, m and n have the meanings given in claims 1 to 6, is reacted with a sulphuric acid derivative of formula III, $$HO_3S—X \qquad (III)$$

wherein X denotes a leaving group which can be substituted by a phenoxide oxygen.

8. A process according to claim 7, wherein the reaction is carried out in the presence of a weak base and a metal iodide.

9. A pharmaceutical composition comprising a compound according to claim 1 and a pharmaceutically acceptable carrier and/or excipient.

10. A method of treating a disease that is responsive to $LTB_4$-antagonistic activity comprising administering to a host in need thereof a therapeutically effective amount of one or more compounds according to claim 1 or the stereoisomers thereof or the acid addition salts thereof.

11. A method according to claim 10, wherein the disease that is treated is selected from arthritis, asthma, chronic obstructive pulmonary disease, psoriasis, ulcerative colitis, gastro- or enteropathy induced by nonsteroidal antiphlogistics, cystic or pulmonary fibrosis, Alzheimer's disease, shock, reperfusion damage/ischaemia, atherosclerosis, multiple sclerosis, autoimmune diseases, malignant neoplasia, alveolitis.

* * * * *

UNITED STATES PATENT AND TRADEMARK OFFICE
CERTIFICATE OF CORRECTION

PATENT NO. : 6,489,359 B2
DATED : December 3, 2002
INVENTOR(S) : Anderskewitz et al.

It is certified that error appears in the above-identified patent and that said Letters Patent is hereby corrected as shown below:

Title page,
Item [30], Foreign Application Priority Data, delete "Dec. 1, 2000" and replace with -- Oct. 24, 2000 --.

Column 10,
Line 7, delete "$X_1$" and replace with -- $X^1$ --.
Line 50, delete "$X_1$" and replace with -- $X^1$ --.

Signed and Sealed this

Fourth Day of March, 2003

JAMES E. ROGAN
*Director of the United States Patent and Trademark Office*